United States Patent [19]

Schlecker et al.

[11] Patent Number: 4,517,196

[45] Date of Patent: May 14, 1985

[54] TRICYCLIC THIAZOLYLOXAMIC ACIDS AND THEIR DERIVATIVES, THEIR PREPARATION, AND THERAPEUTIC AGENTS CONTAINING THESE COMPOUNDS

[75] Inventors: Rainer Schlecker, Bissersheim; Ludwig Friedrich, Bruehl; Dieter Lenke, Ludwigshafen, all of Fed. Rep. of Germany

[73] Assignee: BASF Aktiengesellschaft, Fed. Rep. of Germany

[21] Appl. No.: 411,612

[22] Filed: Aug. 26, 1982

[30] Foreign Application Priority Data

Sep. 5, 1981 [DE] Fed. Rep. of Germany ....... 3135250

[51] Int. Cl.$^3$ ................. C07D 277/60; A61K 31/425
[52] U.S. Cl. .................................... 514/371; 548/150
[58] Field of Search .......................... 548/150; 424/270

[56] References Cited

U.S. PATENT DOCUMENTS 4,069,343  1/1978  Sellstedt ............................... 424/319

FOREIGN PATENT DOCUMENTS

| 6368 | 9/1980 | European Pat. Off. |
| 2413966 | 3/1974 | Fed. Rep. of Germany |
| 2656468 | 12/1976 | Fed. Rep. of Germany |
| 2751441 | 11/1977 | Fed. Rep. of Germany |
| 2828091 | 6/1978 | Fed. Rep. of Germany |
| WO81/01848 | 7/1981 | PCT Int'l. Appl. ................ 548/150 |

OTHER PUBLICATIONS

C.A. 78 No. 23, p. 382, 147943d.
C.A. 45 No. 7, col. 2934, d.

*Primary Examiner*—Robert Gerstl
*Attorney, Agent, or Firm*—Keil & Weinkauf

[57] ABSTRACT

Thiazolyloxamic acids and their derivatives of the general formula I

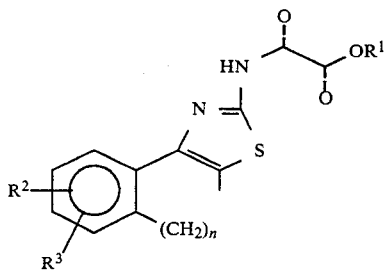

processes for their preparation, and pharmaceutical formulations which contain these compounds and are useful as drugs for treating allergic disorders.

5 Claims, No Drawings

TRICYCLIC THIAZOLYLOXAMIC ACIDS AND THEIR DERIVATIVES, THEIR PREPARATION, AND THERAPEUTIC AGENTS CONTAINING THESE COMPOUNDS

The present invention relates to benzocycloalkanothiazolyloxamic acids and their esters and salts, processes for their preparation, and pharmaceutical formulations which contain these compounds and are useful as drugs for treating allergic disorders.

A number of derivatives of oxamic acid and its esters have been disclosed, for example aryl and hetaryl derivatives in German Laid-Open Application DOS No. 2,413,966, thiazolyl derivatives in German Laid-Open Application DOS No. 2,828,091 and in the Published European Patent Application No. 0,006,368, and benzothiazolyl derivatives in German Laid-Open Applications DOS No. 2,751,441 and DOS No. 2,656,468, and their use for counteracting or suppressing allergic reactions have been described. However, their actions are not always satisfactory.

We have found that compounds of the formula I

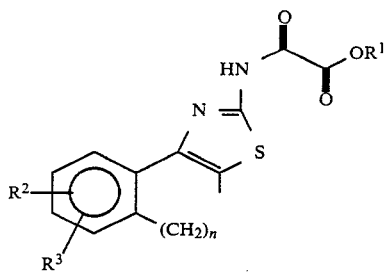

where n is an integer from 1 to 6, and one hydrogen atom in the —$(CH_2)_n$— group may be replaced by lower alkyl of 1 to 6 carbon atoms or by phenyl, or two geminal hydrogen atoms may be replaced by oxygen, $R^1$ is hydrogen or a physiologically tolerated metal or amine cation, or is alkyl of 1 to 6 carbon atoms, $R^2$ and $R^3$ are identical or different and are each hydrogen, fluorine, chlorine, bromine, iodine, nitro or amino, or alkylamino, dialkylamino, acylamino, alkoxy, alkylthio, alkylsulfenyl or alkylsulfonyl where each alkyl is of 1 to 6 carbon atoms, or are each hydroxyl, acyl, cyano or carboxyl, or alkyl of 1 to 5 carbon atoms, possess useful pharmacological properties, in particular as antiallergics.

Preferred compounds of the formula I are those in which n is an integer from 1 to 4, and one hydrogen atom in the —$(CH_2)_n$— group may be replaced by lower alkyl of 1 to 6 carbon atoms or by phenyl, or two geminal hydrogen atoms may be replaced by oxygen, $R^1$ is hydrogen or a physiologically tolerated metal or amine cation, or is alkyl of 1 to 6 carbon atoms, and $R^2$ and $R^3$ are identical or different and are each hydrogen or chlorine, or alkyl or alkoxy where each alkyl is of up to 4 carbon atoms.

Particularly preferred compounds of the general formula I are those in which n is an integer from 1 to 3, and two geminal hydrogen atoms may be replaced by oxygen, $R^1$ is hydrogen or a physiologically tolerated metal or amine cation, or is lower alkyl of 1 to 4 carbon stoms and $R^2$ and $R^3$ are each hydrogen.

The compounds of the general formula I are prepared by a conventional process in which an aminothiazole of the formula II

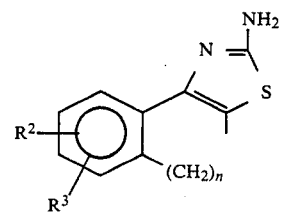

where n, $R^2$, $R^3$ and $R^4$ have the above meanings, is condensed with an alkyloxalyl halide, e.g. ethyloxalyl chloride, or with a dialkyl oxalate, preferably diethyl oxalate, and, if required, the resulting compound is hydrolyzed to give the acid, which is reacted with a physiologically tolerated metal or amine cation to give the salt.

When alkyloxalyl halide is used, the reaction is advantageously carried out at from −30° to 50° C., conventionally at room temperature, in an inert solvent. Examples of suitable solvents are halohydrocarbons, e.g. methylene chloride or chloroform, N-dialkyl carboxamides, e.g. dimethylformamide, cyclic saturated ethers, e.g. tetrahydrofuran or dioxane, and aromatic hydrocarbons, e.g. toluene. The reaction is preferably carried out in the presence of a base, e.g. triethylamine or pyridine.

The reaction of a compound of the formula II with a dialkyl oxalate may be carried out in the presence or absence of a solvent, e.g. toluene, chlorobenzene or diphenyl ether, at from room temperature to the reflux temperature of the reaction mixture.

The alkyl oxamates of the formula I can also be obtained by transesterification of an ester of a low-boiling alcohol, by a conventional process, as described, for example, by Houben-Weyl, vol. 8, pages 526–528.

The oxamic acids of the formula I ($R^1$=H) are prepared by acidic or alkaline hydrolysis of the oxamate in an aqueous or aqueous/alcoholic solution. Examples of suitable bases are sodium hydroxide, potassium carbonate and sodium carbonate, and examples of suitable acids are hydrochloric acid, sulfuric acid and phosphoric acid. The organic acids obtained in this manner may, if required, be converted into their physiologically tolerated amine or metal salts. For the purposes of the invention, these are, for example, salts of the alkali metals, e.g. sodium or potassium, of the alkaline earth metals, e.g. magnesium or calcium, of other metals, e.g. aluminum, of ammonium, or of an organic base, e.g. morpholine, piperidine, mono-, di- or triethanolamine, or tris-(hydroxymethyl)-aminomethane.

A large number of the starting compounds of the formula II are known from the literature, and both these and the compounds which are hitherto unknown may be synthesized by conventional processes, as described in, for example, The Chemistry of Heterocyclic Compounds, Thiazoles and its Derivatives, edited by J. V. Metzger, vol. 1, pages 213 et seq.

Examples of novel compounds, in addition to the compounds described in the examples, are: N-(5-Methyl-8-oxoindeno[1,2-d]thiazol-2-yl)-oxamic acid and its methyl and ethyl esters, N-(5-methoxyindeno-[1,2-d]thiazol-2-yl)-oxamic acid and its methyl, ethyl and isoamyl esters, N-(8-methylindeno[1,2-d]thiazol-2-yl)- oxamic acid and its ethyl ester, N-(6-acetylaminoindeno[1,2-d]thiazol-2-yl)-oxamic acid and its ethyl, propyl and butyl esters, N-(7-aminoindeno[1,2-d]thiazol-2-yl)-oxamic acid and its ethyl and propyl esters, N-(7-methylthioindeno[1,2-d]thiazol-2-yl)-oxamic acid and its methyl, ethyl, propyl and hexyl esters, N-(6-methylsulfenylindeno[1,2-d]thiazol-2-yl)-oxamic acid and its methyl and ethyl esters, N-(5-cyanoindeno[1,2-d]thiazol-2-yl)-oxamic acid and its methyl and ethyl esters, N-(7-methoxybenzo[5,6]cyclohexano[1,2-d]thiazol-2-yl)-oxamic acid and its methyl, ethyl and butyl esters, N-(6-methoxybenzo[5,6]cyclohexano[1,2-d]thiazol-2-yl)-oxamic acid and its methyl, ethyl and isoamyl esters, N-(5-methoxybenzo[5,6]cyclohexano[1,2-d]thiazol-2-yl)-oxamic acid and its methyl, ethyl and propyl esters, N-(8-methylbenzo[5,6]cyclohexano[1,2-d]thiazol-2-yl)-oxamic acid and its methyl, ethyl and pentyl esters, N-(6-chlorobenzo[5,6]cyclohexano[1,2-d]thiazol-2-yl)-oxamic acid and its methyl, ethyl and isoamyl esters, N-(7-nitrobenzo[5,6]cyclohexano[1,2-d]thiazol-2-yl)-oxamic acid and its methyl, ethyl and propyl esters, N-(benzo[6,7]cucloheptano[1,2-yl)oxamic acid and its methyl, ethyl, propyl and isoamyl esters, N-(5,6-dihydroxybenzo[6,7]cycloheptano[1,2-d]thiazol-2-yl)-oxamic acid and its methyl and ethyl esters, N-(8-phenylbenzo[6,7]cycloheptano[1,2-d]thiazol-2-yl)-oxamic acid and its methyl, ethyl and hexyl esters, N-(9-methylbenzo[6,7]cycloheptano[1,2-d]thiazol-2-yl)-oxamic acid and its methyl, ethyl and butyl esters, N-(8-oxobenzo[6,7]cycloheptano[1,2-d]thiazol-2-yl)-oxamic acid and its methyl, ethyl, propyl and butyl esters, N-(benzo[7,8]cyclooctano[1,2-d]thiazol-2-yl)-oxamic acid and its methyl, ethyl, propyl and hexyl esters, N-(7-methylbenzo[7,8]cyclooctano[1,2-d]thiazol-2-yl)-oxamic acid and its methyl, ethyl and isoamyl esters, N-(benzo[8,9]cyclononano[1,2-d]thiazol-2-yl)-oxamic acid and its methyl, ethyl, propyl and butyl esters, N-(4-methylbenzo[8,9]cyclononano[1,2-d]thiazol-2-yl)-oxamic acid and its methyl, ethyl, propyl, butyl and isoamyl esters, N-(benzo[9,10]cyclododecano[1,2-d]thiazol-2-yl)oxamic acid and its methyl and ethyl esters and N-(7-chlorobenzo[9,10]cyclododecano[1,2-d]thiazol-2-yl)-oxamic acid and its methyl, ethyl and isoamyl esters.

The compounds according to the invention possess anti-allergic properties and are therefore useful for the treatment of allergic disorders of the respiratory tract, of the gastrointestinal tract and of the skin, for example for treating allergic asthma, allergic rhinitis and food allergies. In contrast to the conventional antiallergic cromolyn, the novel compounds, when used in animal experiments to treat passive cutaneous anaphylaxia in rats, is found to be effective orally.

The antiallergic action was tested against passive cutaneous anaphylaxis in rats.

Narcotized male rats (weighing from 100 to 140 g) are sensitized by administration of an intradermal injection (shaved skin) of 0.1 ml of an ovalbumin antiserum. After a sensitization period of about 48 hours, treatment is carried out by administering various dosages (10 animals/dose) of the test substances intraperitoneally or orally. 15 and 20 minutes after treatment, an anitgen-/Evans blue mixture (10 mg/kg of ovalbumin in 2% strength Evans blue solution) is injected intravenously into the experimental animals. 30 minutes later, the animals are killed, and the back skin is peeled off and the diameter of the circular blue area on the inner surface is measured. The size of the colored spot in untreated control animals may be standardized. Antiallergic substances reduce the diameter of the colored spots, their reduction being dependent on the dose. The ED 50% is the dose which produces a 50% reduction in the diameter of the colored spot in comparison with control animals which have not been treated with the drug.

The novel compounds have a powerful antiallergic action. As can be seen from Table 1, these compounds, when administered orally, are from 4.4 (Example 2) to 6.6 (Example 4) times more effective than the comparative compound $V_1$ (N-benzothiazol-2-yl oxamate from Example 1 of German Laid-Open Application DOS No. 2,751,441). The recognized commercial preparation cromolyn (Intal ®) is orally ineffective in doses up to 100 mg/kg.

TABLE 1

Antiallergic action after oral administration. Passive cutaneous anaphylaxis (PCA) in rats

| | Inhibition of PCA | |
|---|---|---|
| Example | ED 50% mg/kg | Relative effectiveness |
| 2 | 1.95 | 4.41 |
| 1 | 1.48 | 5.81 |
| 4 | 1.30 | 6.61 |
| $V_1$[1] | >8.60 | 1.00 |
| cromolyn | 100 | — |

[1]N—benzothiazol-2-yl oxamate

The individual therapeutic dose is from 0.1 to 100 mg.

Accordingly, the present invention also relates to therapeutic agents or formulations which in addition to conventional carriers and diluents contain a compound of the formula I as the active compound, and to the use of the novel compounds in the treatment of allergic disorders.

The preferred formulations are those suitable for oral administration. Examples of these are tablets, film tablets, coated tablets, capsules, pills, powders, solutions, suspensions and depot forms. Inhalants and parenteral formulations, e.g. injection solutions, may also be used.

The solid or liquid pharmaceutical forms are prepared in a conventional manner, and to do so the active compounds can be mixed with the conventional pharmaceutical auxiliaries, such as talc, gum arabic, sucrose, lactose, cereal starch or corn starch, potato flour, magnesium stearate, alginates, gum tragacanth, carraghenates, polyvinyl alcohol, polyvinylpyrrolidone, aqueous or non-aqueous carriers, wetting agents, dispersants, emulsifiers and/or preservatives (cf. L. G. Goodman and A. Gilman, the Pharmacological Basis of Therapeutics).

EXAMPLE 1

Ethyl N-(indeno[1,2-d]thiazol-2-yl)-oxamate 4.2 g (0.031 mole) of ethyl chloroformylformate were added dropwise at room temperature to a solution of 5.2 g (0.028 mole) of 2-amino indeno[1,2-d]thiazole in 250 ml of methylene chloride/2.5 ml of pyridine. The reaction mixture was stirred overnight, after which it was washed with water and dried over $Na_2SO_4$, the solvent was distilled off and the residue was recrystallized from acetone to give 5.0 g (62%) of a product of melting point 226°–228° C.

$C_{14}H_{13}N_2O_3S$ (289) calculated: 58.1 C; 4.5 H; 9.7 N. Found: 58.4 C; 4.5 H; 9.8 N.

Starting from the corresponding 2-aminothiazoles and using the same procedure, the following compounds were obtained:

EXAMPLE 2

Ethyl N-(8-oxoindeno[1,2-d]thiazol-2-yl)-oxamate

Yield: 53%, mp. 237°–238° C. (ethyl acetate).

$C_{14}H_{10}N_2SO_4$ (302) calculated: 55.6 C; 3.3 H; 9.3 N. Found: 56.0 C; 3.4 H; 9.2 N.

EXAMPLE 3

Ethyl N-(8-phenylindeno[1,2-d]thiazol-2-yl)-oxamate

Yield: 16%, mp. 177°–179° C.

$C_{20}H_{16}N_2O_3S$ (364) calculated: 65.9 C; 4.4 H; 7.7 N. Found: 65.5 C 4.6 H 7.6 N

EXAMPLE 4

N-(Indeno[1,2-d]thiazol-2-yl)-oxamic acid 3.5 g (0.012 mole) of ethyl N-(indeno[1,2-d]thiazol-2-yl)-oxamate were suspended in a solution of 1.1 g (0.013 mole) of $NaHCO_3$ in 200 ml of water, and the suspension was refluxed for 4 hours. The reaction mixture was filtered, the filtrate was brought to pH 1 with dilute HCl, and the precipitate was filtered off under suction and dried, giving 2.9 g (93%) of a product of melting point 229°–231° C.

$C_{12}H_8N_2O_3S$ calculated: 55.4 C; 3.1 H; 10.8 N. Found: 55.5 C; 3.4 H; 11.1 N.

Examples of pharmaceutical formulations

| Tablets | | |
|---|---|---|
| (a) Active compound | 0.100 g | |
| Stearic acid | 0.010 g | |
| Dextrose | 1.890 g | |
| | 2.000 g | |
| (b) Active compound | 0.020 g | |
| Stearic acid | 0.020 g | |
| Dextrose | 1.960 g | |
| | 2.000 g | |

The constituents are processed in a conventional manner to give tablets of the above composition.

| Inhalant aerosol | |
|---|---|
| Active compound | 1.00 part by weight |
| Soybean lecithin | 0.20 part by weight |
| Aerosol propellent (Frigen 11, 12 and 114) to make up to | 100.00 parts by weight |

The formulation is preferably introduced into an aerosol container which has a metering valve giving a dose of from 5 to 20 mg of active compound when depressed once.

| Ampoules (injection solutions) | |
|---|---|
| Active compound | 50.0 parts by weight |
| Sodium pyrosulfite | 1.0 part by weight |
| Disodium ethylenediamine tetraacetate | 0.5 part by weight |
| Sodium chloride | 8.5 parts by weight |
| double-distilled water to make up to | 1,000.0 parts by weight |

The active compound and the auxiliaries are dissolved in a sufficient amount of water, and the solution is brought to the desired concentration with the required amount of water. The solution is filtered, and introduced into 1 ml ampoules under aseptic conditions. Finally, the ampoules are sterilized and closed, each ampoule containing 50 mg of active compound.

We claim:

1. A compound of the formula I

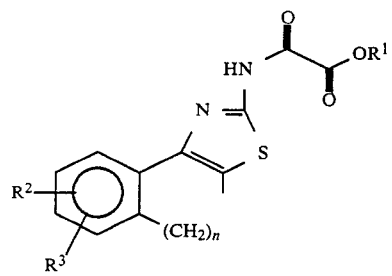

where n is an integer from 1 to 6, and one hydrogen atom in the —$(CH_2)_n$— group may be replaced by lower alkyl of 1 to 6 carbon atoms or by phenyl, or two geminal hydrogen atoms may be replaced by oxygen, $R^1$ is hydrogen or a physiologically tolerated metal or amine cation, or is alkyl of 1 to 6 carbon atoms, $R^2$ and $R^3$ are identical or different and are each hydrogen, fluorine, chlorine, bromine, iodine, nitro or amino, or alkylamino, dialkylamino, acetylamino, alkoxy, alkylthio, alkylsulfenyl or alkylsulfonyl where each alkyl is of 1 to 6 carbon atoms, or are each hydroxyl, acetyl, cyano or carboxyl, or alkyl of 1 to 5 carbon atoms.

2. A compound of the formula I as claimed in claim 1, wherein n is an integer from 1 to 4, and one hydrogen atom in the —$(CH_2)_n$— group may be replaced by lower alkyl of 1 to 6 carbon atoms or by phenyl, or two geminal hydrogen atoms may be replaced by oxygen, $R^1$ is hydrogen or a physiologically tolerated metal or amine cation, or is alkyl of 1 to 6 carbon atoms, and $R^2$ and $R^3$ are identical or different and are each hydrogen or chlorine, or alkyl or alkoxy where each alkyl is of up to 4 carbon atoms.

3. N-(Indeno[1,2-d]thiazol-2-yl)-oxamic acid, its alkyl ester where alkyl is of 1 to 4 carbon atoms, and its salts with a physiologically tolerated metal or amine cation.

4. A composition useful in pharmaceutical dosage unit form for treating allergic disorders which comprises an effective amount of a compound of claim 1, mixed with a pharmaceutical carrier or diluent.

5. A method of treating allergic disorders which comprises administering to the patient an amount of the composition of claim 4 effective to alleviate said allergic disorders.

* * * * *